United States Patent [19]

McKee et al.

[11] Patent Number: 5,510,384

[45] Date of Patent: Apr. 23, 1996

[54] METHOD OF TREATING DAMAGED MUCOSAL AND EPITHELIAL TISSUES WITH MISOPROSTOL

[76] Inventors: Rex N. McKee, 2368 Mill Rd., Traer, Iowa 50675; Frank A. Wingrove, 1029 Sunrise Blvd., Waterloo, Iowa 50701

[21] Appl. No.: 238,646

[22] Filed: May 5, 1994

Related U.S. Application Data

[62] Division of Ser. No. 17,612, Feb. 12, 1993, Pat. No. 5,324,746.

[51] Int. Cl.$^6$ .................................................. A51K 31/445
[52] U.S. Cl. ........................................... 514/530; 514/928
[58] Field of Search .................................... 514/530, 928

[56] References Cited

U.S. PATENT DOCUMENTS

| | | | |
|---|---|---|---|
| 3,965,143 | 6/1976 | Collins et al. | 260/468 D |
| 4,001,286 | 1/1977 | Bundy | 260/410.9 R |
| 4,009,282 | 2/1977 | Voorhees | 424/317 |
| 4,025,645 | 5/1977 | Jelenko, III | 424/312 |
| 4,113,882 | 9/1978 | Okazaki et al. | 424/317 |
| 4,132,738 | 1/1979 | Kluender et al. | 260/586 R |
| 4,181,725 | 1/1980 | Voorhees et al. | 424/258 |
| 4,185,100 | 1/1980 | Rovee et al. | 424/240 |
| 4,201,788 | 5/1980 | Voorhees et al. | 424/304 |
| 4,254,145 | 3/1981 | Birnbaum | 424/305 |
| 4,282,216 | 8/1981 | Rovee et al. | 424/240 |
| 4,353,896 | 10/1982 | Levy | 424/195 |
| 4,360,518 | 11/1982 | Rovee et al. | 424/240 |
| 4,459,310 | 7/1984 | Dajani | 424/305 |
| 4,473,565 | 9/1984 | Rovee et al. | 424/241 |
| 4,515,810 | 5/1985 | Chow et al. | 514/530 |
| 4,707,495 | 11/1987 | Rosenthale et al. | 514/530 |
| 4,840,968 | 6/1989 | Ohnishi | 514/530 |
| 4,889,845 | 12/1989 | Ritter et al. | 514/63 |
| 4,925,873 | 5/1990 | Friedhoff et al. | 514/469 |
| 5,015,481 | 5/1991 | Franz et al. | 424/494 |
| 5,145,686 | 9/1992 | Horrobin et al. | 424/677 |
| 5,167,952 | 12/1992 | McHugh | 424/49 |

OTHER PUBLICATIONS

Meguro, "Chemical Abstracts", CA101(19):164424w, 1984.
Marks et al., "Biosis", BA88:110/, 1988.

*Primary Examiner*—Kimberly Jordan
*Attorney, Agent, or Firm*—Andrus, Sceales, Starke & Sawall

[57] ABSTRACT

A method of treating damaged human tissues, especially mucosal and epithelial tissues, comprising topically administering to the damaged tissues a composition having an effective amount of misoprostol. The treatment is particularly effective against periodontal disease and oral ulcers caused by radiation therapy and chemotherapy.

6 Claims, No Drawings

METHOD OF TREATING DAMAGED MUCOSAL AND EPITHELIAL TISSUES WITH MISOPROSTOL

This application is a divisional of Ser. No. 08/017,612, filed Feb. 12, 1992, now U.S. Pat. No. 5,324,746.

BACKGROUND AND SUMMARY OF THE INVENTION

The present invention relates to a method of treating damaged mucosal and epithelial tissues. More specifically, this invention relates to a treatment comprising the use of misoprostol, an analog of prostaglandin $E_1$.

It is estimated that in the United States alone, there are 140,000,000 adults with periodontal disease in varying forms. Periodontal disease starts as inflammatory lesions because of specific bacteria localizing in the area where the gingiva attaches to the tooth. Usually first to occur is a vascular change in the underlying connective tissue. Inflammation in the connective tissue stimulates the following changes in the epithelial lining of the sulcus and in the epithelial attachment:

1. Increased mitotic activity in the basal epithelial layer.
2. Increased producing of keratin with desquamation.
3. Cellular desquamation adjacent to the tooth surface tends to deepen the pocket.
4. Epithelial cells of the basal layer at the bottom of the sulcus and in the area of attachment proliferate into the connective tissue and break up of the gingival fibers begins to occur.
5. The dissolution of the connective tissue results in the formation of an open lesion.

Proliferation of the epithelial attachment along the root and degeneration of the underlying gingival fibers are primary changes in pocket formation. Proliferation of the epithelial attachment is stimulated by local irritation. Inflammation caused by local irritation producers degeneration of the gingival fibers, periodontal ligament and supporting bone, making it easier for the epithelium to move along the root. The coronal portion of the epithelial attachment detaches from the root as the apical portion migrates. With continued inflammation, the gingiva increases in bulk and the crest of the gingival margin extends toward the crown. The epithelium of the lateral wall migrate along the root and separate from it. The epithelium of the lateral wall of the pocket proliferates to form bulbous and coral-like extensions into the inflamed connective tissue. Leukocytes and edema from the inflamed connective tissue infiltrate the epithelium lining the pocket, resulting in varying degrees of degeneration and necrosis.

Periodontal pockets are chronic inflammatory lesions, and as such are constantly undergoing repair. The condition of the soft tissue wall of the periodontal pocket results from a balance between destructive and constructive tissue changes. The destructive changes consist of the fluid and cellular inflammatory exudate and the associated degenerative changes stimulated by local bacterial infiltrate. The constructive changes consist of the formation of connective tissue cells, collagen fibers and blood vessels in an effort to repair tissue damage caused by inflammation. Healing does not go to completion because of the persistence of local irritants (i.e. bacteria). These irritants stimulate fluid and cellular exudate, which in turn causes degeneration of the new tissue elements formed in the repair process.

Edematous and fibrotic pockets represent opposite extremes of the same pathologic process rather than different disease entities. The outer appearance of a periodontal pocket may be misleading because it is not necessarily a true indication of what is taking place throughout the pocket wall. The severest degenerative changes in periodontal pockets occur along the inner aspect. In some cases inflammation and ulceration on the inside of the pocket are walled off by fibrous tissue on the outer aspect. Outwardly the pocket appears pink and fibrotic despite the degeneration taking place within.

Periodontal pockets contain debris which is principally microorganisms and their products (enzymes, endotoxins and other metabolic products), dental plaque, gingival fluid, food remnants, salivary mucin, desquamated epithelial cells and leukocytes. Plaque-covered calculus usually projects from the tooth surface. If a purulent exudate is present, it consists of living, degenerated and necrotic leukocytes (predominantly polymorphonuclear), living cells and dead bacterial cells, serum and a small mount of fibrin.

The root planing both supra and subgingival with curettage is the basic, most commonly employed procedure for elimination of periodontal pockets and the treatment of periodontal disease. It consists of planing to remove calculus, plaque and other deposits, smoothing the root surface to remove necrotic tooth substances and curetting the inner surface of the gingival wall of the periodontal pockets to separate away diseased soil tissue. The purpose is to accomplish elimination of the pocket by reattachment of connective tissue and epithelium to tooth surface obliterating the pocket or environment for microorganisms to grow. The basic healing processes are the same following all forms of periodontal therapy. They consist of the removal of degenerated tissue debris and the replacement of tissues destroyed by disease. Regeneration is the growth and differentiation of new cells and intercellular substances to form new tissues or parts. It consists of fibroplasia, endothelial proliferation, the deposition of interstitial ground substance and collagen, epithelial hyperplasia and the maturation of connective tissue. Bone and cementum are not replaced by existing bone or cementum, but from connective tissue, which is the precursor of both. Undifferentiated connective tissue cells develop into osteoblasts and cementoblasts which form bone and cementum. Regeneration of the periodontum is a continuous physiologic process. Regeneration is a microscopic activity which differs in degrees from clinically radiographically detectable restoration of destroyed periodontal tissues. Regeneration in most instances restores the continuity of the diseased marginal gingiva and reestablishes a normal gingival sulcus at the same level on the root as the base of the pre-existing periodontal pocket. Reattachment is the re-embedding of new periodontal ligament fibers into new cementum and the attachment of gingival epithelium to tooth surface previously denuded by disease.

The majority of periodontal disease is left untreated primarily because prior to the treatment of the present invention people were subjected to surgical procedures which are painful, alters daily routines for months, is quite expensive and frightens patients away from good therapy. The present misoprostol procedure is very conservative with no surgery. It demonstrates regeneration and reattachment with little discomfort to the patient. The cost is about 25% compared to surgical intervention. The procedure has been shown to improve furcation, establishment of and reattachment and regeneration of tissues between roots of multi-rooted molars, which have always been difficult clinically to maintain and usually cause dentition to be hopeless. Its use as a clinical procedure promises to eliminate a multitude of problems associated with dentition loss, i.e. nutrition, comfort, of a population that ages. Today the statistics are that 43% of the adult population are edentulous by age 55. Because of loss of teeth alveolar bone is also lost in time, meaning loss of the ridge that a denture sets on making a very unstable environment. With the conservative treatment of the present invention the number of edentulous people should be reduced over time plus there should also be a reduction of the amount of money spent on periodontal treatment.

The procedure of the present invention is performed under local anesthesia in a dental office. Curettage and root planing procedures are performed first followed by flushing the wound site with a misoprostol solution. For the following week topical application of misoprostol is applied, typically four times per day. After allowing maturity of the tissue and strict plaque control dramatic changes of pocket depths, inflammation with evidence of regeneration and reattachment of the gum tissue is being found. The procedure of the present invention may also be supplemented with anti-infective coverage using metronidazole 250 mg three times per day for the first week while the clinical disease situation was active and acute.

In summary the method of the present invention provides a new treatment that accelerates healing for the patient, reduces trauma from surgeries that no longer need to be performed, and reduces cost to the patient. Also in necessary surgeries such as gingival grafting it accelerates healing of both the donor site and graft site. Using misoprostol with a local anesthetic such as dyclonine makes the surgical procedures almost painless. Also, a reduction of dry sockets after extractions is being found with the present procedure thus almost eliminating them as a problem in the dental office. The advantage for the periodontal patient is that it eliminates much of the surgery if this process is used on early periodontal cases along with good oral hygiene and maintenance care.

The present treatment has also been found effective to treat oral and paraoral ulcers from radiation and/or chemotherapy. The ulcers commonly develop within days after chemotherapy or radiation therapy. These ulcers usually begin as small, painful irregularly shaped lesions usually covered by a delicate gray necrotic membrane and surrounded by inflammatory tissue. If treatment is not instituted, there many times will be beginning proliferation of tissue around the periphery of the lesion on an inflammatory basis.

This type of ulcer is a non-specific ulcer and microscopically shows loss of continuity of surface epithelium with a fibrinous exudate covering the exposed connective tissue. The epithelium bordering the ulcer usually demonstrates proliferative activity. Polymorphonuclear leukocytes infiltrate in the connective tissue, especially beneath the ulcer. Although if chronic these could be replaced by lymphocytes and plasma cells. Also seen is capillary dilation and its proliferation is evident. Fibroblastic activity may also be prominent with macrophages present in limited numbers.

These lesions because of their size and loss of epithelial integrity lend the body to potential secondary infection. Coupled with the secondary infection, which could eminate from the entire alimentary canal or with chemotherapy ulcers could be widely diverse throughout the alimentary canal, would be loss of weight, potential electrolyte imbalance and dehydration. Routine ingestion of food and water becomes a very painful event and if the ulcers proliferate throughout the alimentary canal diarrhea usually is evident with all its complicating factors.

The therapy disclosed herein using misoprostol both as a troche and as a topical application in an oral adhesive dusted on lesions, has shown dramatic results within 3 to 5 days, allowing a patient to resume good nutrition and proper ingestion of fluids. These same results have occurred with the common canker sore that millions of humans have on a routine basis. Non-specific chronic oral ulcerations may also be treated with this regimen. One patient has had chronic aphthous ulcers without relief for years and was even hospitalized because of them. The misoprostol treatment healed the ulcers completely and for over one year there has been no ulcerative recurrence.

Re-epithelialization occurs rapidly with the use of misoprostol when secondary infection is controlled. The usual course of treatment if signs of secondary infections occurs is to dose with antibiotic and/or antifungals, in addition to misoprostol both as a troche and topically applied with an oral adhesive directly to the lesion. When multiple chemotherapy treatments are administered, the misoprostol is prophylactically used prior to outbreaks of lesions to control them and thus minimize outbreaks or in most cases eliminate lesions.

The effect of chemotherapy and radiotherapy are similar. It is based on the ability to non-specifically destroy or retard the division of rapidly proliferating malignant cells with specific drugs or radiation. Normal cells with rapid turnover, such as oral mucosa or the alimentary canal, are also affected and may result in toxicity and complications. Approximately 20% of patients with cancer are treated with chemotherapy at some time during the course of their disease, also there are approximately 250,000 episodes of oral complications each year. This incidence is likely to increase with the use of more potent drugs and multimodality therapy combining radiation and new chemotherapy.

Control of secondary infections using antibiotics and/or antifungal agents in combination with the present misoprostol routine creates re-epithelialization and inflammation reduction within 3 to 5 days, allowing a patient normal nutrition rather than painful stomatitis. The application is directly to the injured ulcerated tissue by troches or dusting with misoprostol preferably 4 to 5 times daily.

Misoprostol is an analog of prostaglandin $E_1$ and is broken down by most tissues of the body to misoprostol acid, the active metabolyte. Misoprostol has been used in the past on a prescription basis as a gastric mucosa protectant and antiulcer agent. Its primary use is the prevention of nonsteroidal anti-inflammatory drug-induced gastric ulcers, and short term treatment of duodenal ulcers. In contrast, the present method demonstrates a stimulation of re-epithelialization of wounds or damaged mucosal tissues and reduced healing times.

Misoprostol may be administered alone or in combination with other pharmaceutically acceptable agents. Dosages of from not less than about 1 μg per day to no more than about 5 mg per day of the individual compounds per se, or in combinations, are generally effective. In this regard, misoprostol is present in a composition in an amount from about 1 μg to about 1 mg per gram of the composition. Various formulations for the compositions are provided herein. Such formulations may include creams, lotions, ointments, and the like. The compositions and/or formulations may also include additional active ingredients if desired, such as local anesthetics.

The method disclosed herein provides a novel method for the treatment or prevention of a variety of damaged mucosal and epithelial tissues. For example, oral, esophageal, nasal, ocular, aural, anal and genital mucosal tissues may all be treated with misoprostol. It will be evident that the method will find ready application for the prevention or treatment of damaged tissues other than those named, for example dermatological tissues, in which faster wound healing is desired. For example, the treatment of the present invention may also find ready application in severe burn and skin regeneration, skin grafts, pressure sores, diabetic ulcers, fissures, post surgery scar reduction, dry socket, ulcerative colitis, rectal and anal fissures. This treatment also improves healing from dermatological surgery, any surgery involving epithelial tissue, extraction sites or periodontal surgeries.

The present method has the distinct unexpected advantage that it will provide a highly effective treatment for damaged tissues, especially mucosal tissues, and all epithelial tissues, and at the same time this compound advantageously will not produce unwanted systemic or local side effects even if the compound is administered continuously on a daily basis, as long as the appropriate compound dosages are used. It, of course, must be understood that the dosage levels will be adjusted dependent on the response of the subject and the degree of damage to the tissues as monitored by methods known to those skilled in the art.

DETAILED DESCRIPTION OF THE INVENTION

It has now been found that an effective treatment of various damaged tissues, especially mucosal and epithelial tissues, can be achieved with compositions which include an effective amount of misoprostol.

Misoprostol is an analog of prostaglandin $E_1$ in which the carbon 15 hydroxyl group has been removed and replaced by a hydrogen atom, and the two hydrogen atoms at the carbon 16 position have been removed and replaced by a methyl group and a hydroxyl group. Misoprostol may exist in either the 16R- or 16S- stereoisomeric forms. Structurally, these analogs are characterized by the general formula I or II shown below:

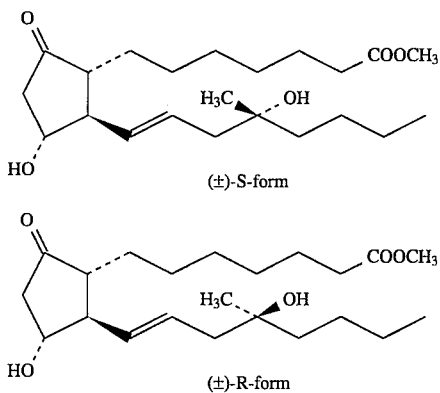

The present method of treating damaged human tissues, especially mucosal and epithelial tissues, comprises topically administering to a subject having the damaged tissues a composition having an effective amount of misoprostol. Topical application involves administering an effective daily dose of misoprostol in an amount of from about 1 μg to about 1 mg per gram of the composition which effectively administers 1 μg to about 5 mg misoprostol per day for a desired period, i.e. typically at least four days. The preferred dosage range is dependent upon the particular wound or damaged tissue being treated and the response of the patient to treatment, as is well known by those skilled in the art. For example, preferred ranges for the treatment of damaged oral tissues caused by periodontal disease might be 4 μg per day to about 800 μg per day while the preferred ranges for the treatment of ulcers caused by radiation therapy and/or chemotherapy might be about 4 μg per day to about 1 mg per day.

Misoprostol used in the method of this invention may be synthesized in accordance with known procedures. Accordingly, a description of a method for the preparation of misoprostol is deemed unnecessary herein.

The method disclosed herein may be utilized to treat oral, esophagal, nasal, ocular, oral, anal and genital mucosal tissues. It has been found that misoprostol is particularly effective in the treatment of damaged oral mucosal tissues. For example, misoprostol has been found particularly effective against damaged tissues caused by periodontal disease as well as ulcers caused by radiation therapy and/or chemotherapy. Inflammatory lesions as well as periodontal pockets have also been effectively treated.

Compositions for use in the above-mentioned treatment of damaged mucosal tissues comprise an effective amount of misoprostol as the active ingredient and a suitable carrier. As previously noted herein, an effective amount of misoprostol for use in accordance with this invention is from about 1 μg to about 1 mg per gram of composition. A concentration of about 240 μg per gram of composition is preferred.

The topical compositions of this invention are formulated preferably as creams, lotions, ointments and the like by choice of appropriate carriers. Suitable carriers include vegetable or mineral oils, white petrolatum (white soft paraffin), branched chain fats or oils, animal fats and alcohols such as absolute ethanol. The preferred carriers are those in which the active ingredient is soluble. Emulsifiers, stabilizers and anti-oxidants may also be included as well as agents imparting color or fragrance if desired.

Creams are preferably formulated from a mixture of mineral off, self-emulsifying beeswax and water in which mixture the active ingredient, dissolved in a small amount of an oil such as almond oil, is admixed. A typical example of such a cream is one which includes about 40 parts water, 20 parts beeswax, 39 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil, and about 70% white soft paraffin by weight.

Lotions may be conveniently prepared by dissolving the active ingredient, in a suitable high molecular weight alcohol such as propylene glycol or polyethylene glycol.

It should be recognized that misoprostol will break down to prostaglandin A if in the presence of water. Thus, creams last approximately only one week because of this stability problem. Therefore, misoprostol is best used in a powder form that can be hydrated at the time of use. Misoprostol is more stable in a vehicle that uses propylene glycol. It can be stored in a dry state for a couple years if it is stabilized with hydroxypropyl methyl cellulose. In liquid form as the oil it is preferably dissolved in absolute alcohol (ethanol) and frozen. The frozen alcohol and misoprostol mixture is stable for at least a year.

One or more additional substances which have therapeutic effects on the skin and/or tissue being treated may also be incorporated in the composition. For example, other suitable types of active ingredients may be incorporated in the compositions of this invention and may include other compounds known to have beneficial effect on skin and/or mucosal tissue. Additionally, anti-inflammatory agents as well as local anesthetics such as dyelonine in an amount of about 0.5 to 1% by weight.

The proportions of the misoprostol compound, or each of the compounds in the composition, are dependent upon the particular wound or damaged tissue being addressed and the degree of response desired. Amounts in excess of about 5 mg per day of misoprostol or the combination of that compound with other pharmaceutically acceptable compounds, are generally unnecessary to achieve the desired results, and may not be economically sound practice. In practice the higher doses are used where therapeutic treatment of the wound or damaged tissue is the desired end while the lower doses are generally used for prophylactic or maintenance purposes, it being understood that the specific dosage administered in any given case will be adjusted in accordance with the specific compounds being administered, the damaged tissue to be treated, the condition of the subject and other relevant medical facts that may modify the activity of misoprostol or the response to the subject, as is well known by those skilled in the art. In general, either a single daily dose or divided daily dosages may be employed, as is well known in the art.

Dosage forms of the compound can be prepared by combining them with a non-toxic pharmaceutically acceptable carrier to make either immediate or slow release formulations as is well known in the art. Such carriers may be either solid or liquid in form such as, for example, cornstarch, lactose, sucrose, peanut oil, olive oil, sesame oil, propylene glycol and water. If a solid carrier is uses the dosage forms of the compound of the invention may be powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

The treatment for periodontal disease involves a removal of calculus from the tooth and the root. The cleaned area is then irrigated one time only, with a saline solution of misoprostol. Additional topical treatments are administered by blowing an oral adhesive powder containing about 0.004% to about 0.1%, preferably 0.024% misoprostol on the gum and the margins of the tooth and gum of the procedure area. This topical powder application provides a prolonged contact to a localized site with a high misoprostol concentration, and is preferably done four times daily for about 7 days.

Topical powder application of the misoprostol to the gum and tooth area is preferably accomplished by applying misoprostol mixed in an oral adhesive. The oral adhesive may be composed of polyox WSR-301 10% and hydroxypropyl methylcellulose 90% with misoprostol incorporated to make a 0.024% W/W powder mixture. Polyox WSR-301 functions as an adhesive, and the mixture when sprayed on the gum hydrates to form an adhesive gel that maintains a prolonged contact with the treatment site. The powder is puffed on the target site with a collapsible bottle with an applicator tip. The direct topical application to a target area delivers a high concentration of misoprostol which gradually leaches out of the hydrated gel into the covered tissue.

Treatment of oral lesions or oral mucosal breakdown is preferably of two types. First, for areas of localized involvement, misoprostol, preferably 0.024%, is topically applied in powder form directly on the affected site. The powder hydrates and forms an adhesive gel that adheres to the target area of the gum, tongue or oral mucosa. Treatments are preferably applied three to four times daily until the problem disappears. Secondly, when the involved areas of the mouth and esophagus are either too numerous or difficult to be reached by a powder application, oral misoprostol 200 mcg troches are preferably used. These are lozenges made with polyethylene glycol 1450. The patient is instructed to slowly dissolve the troche in the mouth two to four times daily until the problem is resolved. The troche in a demulcent effect coats the mucous membranes with the misoprostol.

Topical application of compositions containing misoprostol was found to be therapeutically effective in field studies. In a typical example, topical application of an oral adhesive powder containing 0.024% misoprostol to the damaged tissue four times daily for seven days resulted in improved and/or healed tissues. The following examples illustrate the efficacy of compositions containing misoprostol in accordance with the present invention.

EXAMPLE 1

The following topical powder was formulated for use in connection with the topical treatment of oral mucosa:

| | |
|---|---|
| 6 Misoprostol 200 mcg tablets ground to a fine powder. | |
| Polyox WSR-301 | 0.373 gm |
| Methocel E4M Premium | 3.313 gm |
| (Hydroxypropylmethylcellulose) | |
| Dyclonine | 0.05 gm |

This powder is triturated well and mixed until uniform. Then it is put into a 30 ml collapsible bottle. The collapsible bottle is used to puff the powder through its applicator tip to the desired area in the mouth. Three very light applications are done with the patient taking a drink of water after each application. The powder hydrates and forms a viscous gel that stays localized to the area for a prolonged period of time. The Dyclonine is a local anesthetic which deadens the area. The misoprostol application to gum tissue results in a rapid epithelization. Application is preferably four times daily.

EXAMPLE 2

The misoprostol irrigation solution used in the initial step of treating periodontal disease is made by grinding tablets containing 1.2 mg of misoprostol and adding 3 ml of absolute ethyl alcohol. The resulting suspension is shaken for 30 minutes and let stand in a closed test tube for one hour and then centrifuged. The clear solution is drawn off with a syringe and cold sterilized by being pushed through a 0.2 micron sterile filter into a sterile vial using sterile technique in a lamnar flow hood. 1 ml of the alcoholic-misoprostol solution is added to 14 ml of sterile saline for injection at the time of the irrigation procedure. This solution will deliver about 30 mcg of misoprostol per milliliter.

EXAMPLE 3

The following topical cream was formulated for use in connection with the topical treatment of burns to the skin due to radiation oncology:

6 misoprostol 200 mcg tablets ground into a fine powder. Wet powder with propylene glycol to make a smooth paste and incorporate enough aquaphilic ointment to make 5 gm of cream.

This formulation is preferably applied sparingly to the involved area twice daily.

EXAMPLE 4

To treat radiation burns of the mouth and esophagus, misoprostol troches 200 mcg were formulated as follows:

| Misoprostol 200 mcg tablets | #100 |
|---|---|
| Nutrasweet | 2.08 gm |
| Silica Gel Micronized | 1.0 gm |
| Acacia Powder | 1.664 gm |
| Xanthan Gum | 0.540 gm |
| PEG 1450 | 88.0 gm |

This is the formula for 100 troches. The troche is preferably melted in the mouth four times daily. This has greatly reduced the oral and esophageal mucosal damage and pain, and reduced the number of times radiation therapy had to be stopped due to the patient being unable to endure the pain or unable to eat or drink. This formulation might also be used for auto-immune diseases like aphthous ulcers, lichens plantus, pemphigus, epidermolysis, lupus lesions, pemphigus vulgaris, pemphigus foliaceus, pemphigus vegetans, pemphigus erythematous, benign mucous membrane pemphigus, and desquamative lesions.

The following case histories are presented to demonstrate the efficacy of the present treatment, and the breadth of possible applications:

EXAMPLE 5

On Oct. 1, 1992 patient #1 was presented with severe oral ulcers, including mucous membranes, tongue, uvula. The ulcers were large ulcers, 2 cm long and 1 cm wide. Gave misoprostol 0.024%—Dyclonine 1% treatment which continued for 5 days. Upon examination on Oct. 8, 1992 there were no ulcerations. Previously patient #1 had not been able to eat or drink. All lesions had healed to a point that the only clinically visible signs were slight areas of redness. Continued treatment involved using puffer in morning and evening and misoprostol troches during day.

EXAMPLE 6

Patient #2 developed ulcers from chemotherapy. On Sep. 19, 1992 there was observed multiple areas of mucoid degeneration some ulcers 1.5 cm in diameter. Applied misoprostol 0.024%—Dyclonine 1% powder on lesion. Checked patient again on Sep. 29, 1992 and observed lesions. All had healed showing no open lesion with only clinical evidence of redness. Will continue misoprostol powder treatment until all lesions healed.

EXAMPLE 7

Patient #3 was a long term patient with degenerative gingivitis. At times showing severe slough of epithelium to a point of bleeding; problem drinking and eating. Patient #3 had been treated with asteroid which was giving side effects. On Jul. 10, 1992 misoprostol 0.024%—Dyclonine 1% powder was dispensed with instructions to use once at night before bed.

On Jul. 17, 1992 patient was checked. Tissue appeared smooth and healthy with slight redness. Patient stated felt normal.

On Aug. 28, 1992 patient was re-checked. Tissue continued to improve.

On Oct. 9, 1992 patient was again checked. Less bleeding, but still slight redness. Marked improvement from previous treatment with steroid.

EXAMPLE 8

Patient #4 was presented with lack of attached gingivae. On Jul. 14, 1992 a sliding graft was performed. Patient given misoprostol 0.024%—Dyclonine 1% powder to dust surgery area. On Jul. 21, 1992 the sutures were removed. Patient stated no pain. Surgical site demonstrated marked healing, and was estimated about one week ahead of normal.

EXAMPLE 9

Patient #5 presented with chronic canker sores. Had been hospitalized for 2 weeks because of loss of electrolytes, dehydration and poor nutrition from oral sores. On Mar. 10, 1992 gave misoprostol 0.024%—Dyclonine 1% powder and troches. On Mar. 27, 1992 no canker sores. Patient states first time in years that she feels this good. Patient uses the medication when she first feels a sore even before it breaks open and has been able to prevent them from occurring. Patient checked on May 26, 1992. Had run out of misoprostol. Noted a canker sore lower left. Placed back on medication.

Patient rechecked on Jun. 5, 1992. Sore gone. Will continue with misoprostol as needs occur. Patient checked on Jun. 18, 1992. All areas responding. On Jul. 7, 1992 patient had reoccurrence of canker sores, and was re-started on powder and troches. Patient checked on Jul. 10, 1992. Sores gone. Patient checked again on Sep. 22, 1992 and showed no sores. Patient checked on Oct. 1, 1992 and no sores were found.

We claim:

1. A method of treating damaged mucosal and epithelial tissues comprising topically administering to the damaged tissue a composition having an effective amount of misoprostol, said mucosal tissue selected from the group consisting of oral, nasal, ocular, aural, anal and genital tissues.

2. The method of claim 1 wherein said effective amount comprises from about 1 µg to about 1 mg misoprostol per gram of the composition.

3. The method of claim 1 wherein said mucosal tissue is an oral tissue and the damaged tissues are caused by periodontal disease.

4. The method of claim 1 wherein said mucosal tissue is an oral tissue and the damaged tissues are ulcers caused by radiation therapy.

5. The method of claim 1 wherein said mucosal tissue is an oral tissue and the damaged tissues are ulcers caused by chemotherapy.

6. The method of claim 1 wherein said mucosal tissue is an oral tissue and the damaged tissues are inflammatory lesions.

* * * * *